United States Patent [19]
Yam

[11] Patent Number: 5,855,873
[45] Date of Patent: Jan. 5, 1999

[54] STABLE SOLUTION OF ZINC AND BICARBONATE IONS

[75] Inventor: Benny S. Yam, Holmdel, N.J.

[73] Assignee: Church Dwight & Co., Inc., Princeton, N.J.

[21] Appl. No.: 957,904

[22] Filed: Oct. 27, 1997

[51] Int. Cl.$^6$ .............. A61K 7/16; A61K 7/36; A61K 31/315; A61K 33/30
[52] U.S. Cl. ............ 424/49; 424/642; 424/717; 424/67
[58] Field of Search ......................... 424/49–58

[56] References Cited

U.S. PATENT DOCUMENTS

| | | | |
|---|---|---|---|
| 3,887,704 | 6/1975 | Lichtenstein | 424/145 |
| 4,289,755 | 9/1981 | Dhabhar | 424/52 |
| 4,292,324 | 9/1981 | Jönsson et al. | 424/145 |
| 4,312,889 | 1/1982 | Melsheimer . | |
| 4,568,540 | 2/1986 | Asano et al. | 424/52 |
| 4,666,708 | 5/1987 | Goldemberg et al. . | |
| 4,992,259 | 2/1991 | Schiraldi et al. | 424/49 |
| 5,076,960 | 12/1991 | Hutchings et al. | 252/186.33 |
| 5,182,099 | 1/1993 | Jonsson et al. | 424/49 |
| 5,185,153 | 2/1993 | Pollock . | |
| 5,302,373 | 4/1994 | Giacin et al. | 424/49 |
| 5,330,749 | 7/1994 | Giacin et al. . | |
| 5,455,023 | 10/1995 | Giacin et al. . | |
| 5,456,902 | 10/1995 | Williams et al. . | |
| 5,541,165 | 7/1996 | Turgeon . | |
| 5,554,358 | 9/1996 | Williams et al. . | |
| 5,587,147 | 12/1996 | Domke et al. | 424/49 |
| 5,616,313 | 4/1997 | Williams et al. | 424/49 |
| 5,632,972 | 5/1997 | Williams et al. | 424/49 |
| 5,753,217 | 5/1998 | Christopher | 424/53 |

*Primary Examiner*—Shep K. Rose
*Attorney, Agent, or Firm*—Irving Fishman

[57] ABSTRACT

A storage stable aqueous or aqueous/alcoholic solution of zinc ions in the presence of bicarbonate ions is disclosed. The solution comprises: (a) a source of zinc ion, (b) a source of a stabilizing anion which can stabilize soluble zinc and bicarbonate in solution; (c) a source of bicarbonate ion; and (d) a solvent therefor. The solvent comprises: (i) a major proportion of water; (ii) optionally a minor amount of a lower monohydric alcohol; and (iii) optionally a minor amount of a humectant having at least 3 hydroxy groups. The zinc salt is present in an amount A sufficient to provide from about 0.01 weight % to about 1 weight % zinc ion; the stabilizing anion in an amount B of at least 1.2 equivalents per equivalent of zinc ion; and the bicarbonate ion cannot exceed certain levels which are related to the level of the stabilizing anion.

14 Claims, No Drawings

STABLE SOLUTION OF ZINC AND BICARBONATE IONS

CROSS-REFERENCE TO RELATED APPLICATIONS

Not Applicable

STATEMENT REGARDING FEDERALLY SPONSORED RESEARCH OR DEVELOPMENT

Not Applicable

FIELD OF THE INVENTION

The present invention relates generally to solutions of zinc containing compounds in the presence of bicarbonate ions. The invention relates in particular to mouthwashes containing zinc and bicarbonate ions in solution.

BACKGROUND OF THE INVENTION

Zinc ion has been used in oral products for some time now. In dentrifices, it has been employed as a tartar control agent. In mouthwashes, it is used as a bacteriocide (U.S. Pat. No. 5,455,023) and to combat malodor.

Bicarbonate has been used in oral products for a variety of purposes including, but not limited to, buffering capacity, alkalinizing agent, as an abrasive (as solid sodium bicarbonate particles), for deodorizing activity, and because it provides for a clean "mouthfeel" and a refreshing aftertaste in the oral cavity. Exemplary patents dealing with mouthwashes or rinses having bicarbonate included include, but are not limited to U.S. Pat. No. 4,132,770; U.S. Pat. No. 4,312,889; U.S. Pat. No. 4,666,708; U.S. Pat. No. 5,185,153; U.S. Pat. No. 5,302,373; U.S. Pat. No. 5,330,749, U.S. Pat. No. 5,455,023; U.S. Pat. No. 5,541,165; and U.S. Pat. No. 5,587,147; all of which are incorporated herein by reference.

It has therefore been deemed advantageous to try to combine, in a single formulation, both zinc containing compounds and bicarbonate containing compounds. Unfortunately this has not been possible. Zinc ion reacts with bicarbonate ion to result in liberation of carbon dioxide and the formation of various insoluble basic salts of zinc and carbonate. Attempts to get around this technical difficulty have included keeping the two components separated in different compartment or containers until ready for use; encapsulating one or both of the ingredients; or presenting one or both of the components in slightly soluble form so that the two species are in limited contact until diluted by the user in the course of using the product, among others.

Examples of encapsulating one or both components include U.S. Pat. No. 5,302,373; U.S. Pat. No. 5,330,749; and U.S. Pat. No. 5,455,023. Examples of dual compartment dispensing include U.S. Pat. No. 5,456,902; U.S. Pat. No. 5,554,358; U.S. Pat. No. 5,616,313; and U.S. Pat. No. 5,632,972. Examples of complexation include U.S. Pat. No. 5,587,147. Typical of the presentation of one or more of the components in an insoluble or slightly soluble form until use is in the toothpaste, tooth gel and tooth powder area where remaining in solution during storage is not a critical requirement to meet.

However, mouthwashes cannot present with precipitates during storage and still be considered suitable delivery vehicles for the components they contain. Additionally, dual dispensing systems are inconvenient for the user and generally not desirable. As such, there has been a long felt need for a single phase stable mouthwash solution having both zinc ion containing compounds and bicarbonate ion containing compounds, each in solution.

OBJECTS OF THE INVENTION

It is therefore an object of the invention to provide a single phase, stable mouthwash solution having both zinc ion containing compounds and bicarbonate ion containing compounds, each in solution.

It is another object of the invention to provide a single phase stable mouthwash solution having both zinc ion containing compounds and bicarbonate containing compounds, each in solution, in amounts which are effective for the prevention and/or counteracting oral malodors.

It is another object of the invention to provide a single phase stable solution having both zinc ion containing compounds and bicarbonate containing compounds, each in solution, in amounts which are effective in the treatment and/or prevention of dental tartar, plaque, and/or gum disease.

Still other objects of the invention will be appreciated by those of ordinary skill in the art.

BRIEF SUMMARY OF THE INVENTION

These and other objects of the invention can be achieved by a storage stable aqueous or aqueous/alcoholic solution of zinc ions in the presence of bicarbonate ions comprising:
(a) a zinc ion source;
(b) a source of a stabilizing anion which stabilizes solutions of zinc ions in the presence of bicarbonate ions;
(c) a bicarbonate ion source; and
(d) a solvent therefor, said solvent comprising:
  (i) a major proportion of water;
  (ii) optionally a minor amount of a lower alkyl monohydric alcohol; and
  (iii) optionally a minor amount of a humectant having at least 3 hydroxy groups;
said stabilizing anion being selected from anions of organic di-, tri, and poly-acids and di-, tri, and poly-phosphates;
said zinc ions being present in an amount A of from about 0.01 to about 1 weight %;
said stabilizing anion present in an amount B, which is at least 1.2 equivalents per equivalent of zinc ion;
said bicarbonate being present in an amount of C equivalents, which is no greater than the sum of
  (a) (6)×(the number of equivalents of said anions of di-, tri-, or poly-phosphates); and
  (b) $\{(3^{(n-1)})/(2^m)\}$×(the number of equivalents of said anions of organic di-, tri-, or poly- acids), where n is the number of carboxyl groups and m is the number of basic nitrogens, if any.

BRIEF DESCRIPTION OF THE SEVERAL VIEWS OF THE DRAWING

Not Applicable

DETAILED DESCRIPTION OF THE INVENTION

The present invention is directed to a single phase storage stable solution of a zinc salt and a bicarbonate salt. It is well known that zinc ion and bicarbonate ion will interact in solution to ultimately form insoluble zinc carbonate. Since it is desirable to have both zinc ion and bicarbonate ion present in the same solution for a variety of purposes, creating a storage stable solution of these species has been long sought after. The present invention accomplishes this desired result.

The invention results in a storage stable single phase solution of these ions by combining a zinc ion source, a source of a stabilizing anion, and a bicarbonate source, in a vehicle which is predominately water. Optional components of the vehicle in addition to the water include a lower alkyl monohydric alcohol and/or a humectant having at least 3 hydroxy groups per molecule. Other components which may be present include antibacterial agents, surfactants, viscosity enhancers, sweeteners, flavors, and/or colors.

More specifically, the invention is a storage stable aqueous or aqueous/alcoholic solution of zinc ions in the presence of bicarbonate ions which results from providing, in a single solution:

(a) a zinc ion source;
(b) a source of a stabilizing anion which stabilizes solutions of zinc ions in the presence of bicarbonate ions;
(c) a bicarbonate ion source; and
(d) a solvent therefor, said solvent comprising:
 (i) a major proportion of water;
 (ii) optionally a minor amount of a lower alkyl monohydric alcohol; and
 (iii) optionally a minor amount of a humectant having at least 3 hydroxy groups;

said stabilizing anion being selected from anions of organic di-, tri, and poly-acids and di-, tri, and poly- phosphates; said zinc ions being present in an amount A of from about 0.01 to about 1 weight %, preferably about 0.04 to about 0.5 weight %, more preferably about 0.08 to about 0.25 weight %, most preferably about 0.12 weight %; said stabilizing anion present in an amount B, which is at least 1.2 equivalents per equivalent of zinc ion; said bicarbonate being present in an amount of C equivalents, which is no greater than the sum of (a) (6)×(the number of equivalents of said anions of di-, tri-, or poly-phosphates); and
(b) $\{(3^{(n-1)})/(2^m)\}$×(the number of equivalents of said anions of organic di-, tri-, or poly- acids), where n is the number of carboxyl groups and m is the number of basic nitrogens, if any.

The zinc source can be any zinc containing compound which is acceptable for the ultimate utility to which the solution is intended. Hence, in the mouthwash field, the zinc source, as well as the other components must be selected from orally acceptable zinc compounds. This restriction is not required when the solution is being prepared for conversion of the compounds in other reactions and are not intended to be used in or on the body. Those of ordinary skill in these fields will appreciate such distinctions in applying the invention more broadly than in the preparation of mouthwashes. For example, where zinc containing compounds are utilized in other applications, such as in deodorants or shampoos, and it is desirable to have bicarbonate ion also present, and maintain the zinc and bicarbonate in solution, the components need only be acceptable for deodorant or shampoo application and need not be limited to orally acceptable.

Preferably, the zinc source can be selected from commonly available compounds, such as salts of zinc with one or more anions selected from the group consisting of chloride, sulfate, monophosphate, di- or higher polyphosphate (including but not limited to pyrophosphate, metaphosphate, tripolyphosphate, tetrametaphosphate, and orthophosphate, and anions of mono-, di-, tri-, or poly- organic acids. Of the phosphates, tripolyphosphate is preferred. Of the organic acids, gluconate, tartrate, fumarate, maleate, malonate, malate, lactate, citrate, EDTA (ethylenediaminetetraacetic acid), citraconate, citramalate, stearate, oleate, laurate, octoate ascorbate, picolinate, and orotate are quite suitable; however, the anions of di-, tri, and poly- organic acids are preferred, with tartrate, citrate, and EDTA being more preferable. The most highly preferred anion in the zinc source is citrate. Mixed salts, i.e. those of zinc with more than one of these anions, or zinc and another acceptable cation with one or more of these anions, are also suitable sources of zinc ion in the present invention. Such mixed salts include without limitation: sodium zinc citrate, magnesium zinc citrate, and zinc stearatelaurate for example.

The stabilizing anion is selected from phosphates having more than one —(P=O)— group and organic acids having more than one acid functionality. While it is not impossible to add these materials as free acids, if the resulting pH is too low, the acidity will result in destruction of the bicarbonate ion. Hence, these are generally added as soluble salts of the acids, usually as the alkali metal salts, although any acceptable soluble salt may be used. The stabilizing anions suitable in this invention include the non-organic phosphates such as di-, tri-, and higher poly- phosphates; and the anions of di-, tri-, and higher poly- organic acids, such as tartrate, fumarate, maleate, malonate, malate, citraconate, citramalate, lactate, citrate, EDTA (ethylenediaminetetraacetic acid) and the corresponding compounds wherein one or more of the carbonyl groups (—(C=O)—O—) are replaced by —(PO$_4$)— groups. Preferably the stabilizing anion is selected from the group consisting of tripolyphosphate, tartrate, citrate, and EDTA; more preferably, it is citrate. While the cation for the stabilizing anion source can be virtually any suitable cation, it is preferably an alkali metal or magnesium, more preferably sodium or potassium, most preferably, sodium.

While the anion from the zinc source and the stabilizing anion may be different, they are preferably the same.

The bicarbonate source is typically an alkali metal or magnesium bicarbonate, more preferably sodium or potassium bicarbonate, most preferably, sodium bicarbonate.

It is well known that solubilized zinc ion and bicarbonate ion will react with other to form insoluble zinc carbonate. Both of these species are present in the present invention. I have now found that the presence of a stabilizing anion and the observance of molar equivalent ratios between the zinc and the stabilizing anion AND between the stabilizing anion and the bicarbonate ion permits both the zinc ion and the bicarbonate ion to coexist in solution in a single phase.

The ratio of molar equivalents of stabilizing anion to equivalents of zinc ion must exceed 1.2:1. Preferably it is greater than about 1.4:1, more preferably greater than about 1.6:1.

The ratio of molar equivalents of bicarbonate ion to stabilizing anion must be such that the bicarbonate ion equivalents does not exceed the sum of:

(a) (6)×(the number of equivalents of said di-, tri-, or poly-phosphates); and
(b) $\{(3^{(n-1)})/(2^m)\}$×(the number of equivalents of said anions of organic di-, tri-, or poly- acids), where n is the number of carboxyl groups and m is the number of basic nitrogens, if any.

Preferably, portion (a) of the above sum is not greater than about 4×(the number of equivalents of said di-, tri-, or poly- phosphates). Preferably portion (b) of the above sum is not greater than about $\{(2.9^{(n-1)})/(2^m)\}$×(the number of equivalents of said anions of organic di-, tri-, or poly- acids).

The solvent may be totally water. In the mouthwash field, the solvent may also be plain water or may be water as a major component with minor components of either or both of a lower alkyl monohydric alcohol or a humectant having at least 3 hydroxy groups. Other variations on the theme for other applications of this invention will be apparent to those of ordinary skill in their respective fields.

Lower alkyl monohydric alcohols for the invention in the mouthwash field are suitably selected from $C_{1-4}$ alkanols, preferably $C_{2-3}$ alkanols, most preferably ethanol. The alkanols may be either straight chain or branched. When present, the alkanol can be present up to about 30% of the formulation, preferably up to about 25% of the formulation, more preferably about 10 to about 20% of the formulation, still more preferably about 12 to about 15% of the formulation.

The humectant for the invention in the mouthwash field is typically a $C_{3-6}$ compound having at least 3 hydroxy groups. Typical humectants suitable in this invention include, but not limited to, glycerin and sorbitol. When present, the humectant may be present up to about 20% of the formulation, preferably up to about 15% of the formulation, more preferably from about 7 to about 11% of the formulation, most preferably about 9% of the formulation.

In addition, in the mouthwash field, other mouthwash standard ingredients such as surfactants, such as those in the PLURONIC series, especially PLURONIC F-127, antibacterials, such as cetylpyridiniumchloride, flavors, sweeteners, such as sodium saccharine, colors, fragrances, and thickeners, such as carboxymethylcellulose, may be added as well. When present, the surfactants are used preferably in amounts of up to about 2 weight %; the antibacterials are used in antibacterial effective amounts preferably of up to about 2 weight %; the flavors are used preferably in amounts of up to about 1 weight %, the sweeteners preferably in amounts of up to about 0.6 weight %; the thickeners are used in amounts sufficient to obtain the desired viscosity, preferably in amounts of up to about 0.5 weight %; the colors are preferably used in amounts of up to about 0.25 weight % and the fragrances are preferably used in amounts of up to about 1 weight %; all based on the total formulation. The upper limits on these auxiliary non-essential components may be exceeded when desired without departing from the invention.

The various components may be added in essentially any order, but it is highly preferable that the zinc source and the necessary amount of stabilizing anion be brought together in solution prior to contacting the zinc source with the bicarbonate source. This promotes realizing the desired effect more quickly. If the order is reversed and the bicarbonate is contacted with the zinc source in solution before the stabilizing anion is contacted with the zinc source in solution, there is greater risk that insoluble zinc carbonate will result and the resolubilization of the zinc carbonate takes considerable time.

In general, the stabilizing anion is dissolved in the water, with mixing until the solution is clear. The zinc source is then added with mixing until the solution is clear. The remaining ingredients, other than the alcohol, surfactant and the flavors are added with stirring until clear. The surfactant and flavors are dissolved in the alcohol and the alcoholic mixture is added to the otherwise complete formulation.

EXAMPLES

Example 1

The following formulations are prepared in the manner set forth below, with the components as set forth in the table below, to yield invention Product A and non-invention Products B and C:

| | Amount (% by weight) | | |
|---|---|---|---|
| Component | Product A | Product B | Product C |
| Zinc Citrate Trihydrate | 0.38 | 0.38 | 0.38 |
| Sodium Citrate Dihydrate | 1.00 | 0.15 | 1.00 |
| Sodium Bicarbonate | 3.00 | 3.00 | 4.75 |
| Water | 73.59 | 74.44 | 71.84 |
| Ethanol | 12.00 | 12.00 | 12.00 |
| Glycerin | 9.00 | 9.00 | 9.00 |
| Pluronic F-127 | 0.45 | 0.45 | 0.45 |
| Cetyl Pyridinium Chloride | 0.10 | 0.10 | 0.10 |
| Flavor | 0.25 | 0.25 | 0.25 |
| Sodium Saccharine | 0.12 | 0.12 | 0.12 |
| Carboxy Methyl Cellulose | 0.06 | 0.06 | 0.06 |
| Color | 0.05 | 0.05 | 0.05 |

An aqueous phase mixture is prepared by first adding the sodium citrate to the water with mixing until clear. Next the zinc citrate is added to the aqueous phase with mixing until clear. The carboxymethylcelluloise is dispersed in the glycerine and this dispersion is added to the aqueous phase, along with the sodium saccharin, cetyl pyridinium chloride, and color, with mixing until the solution is clear The sodium bicarbonate is then added to the aqueous phase with mixing until the solution is clear. An alcoholic phase is prepared separately by adding the Pluronic and the flavor to the ethanol with mixing until the solution is clear. The resulting alcoholic solution is added to the aqueous phase with mixing until the solution is clear to yield the final product.

Example 2

Each of Products A–C are subjected to accelerated stability studies at 122° F. for a period of 4 weeks. The products are examined for the presence of insoluble crystals at different time intervals. Samples are taken after 12 days and after 4 weeks and analyzed for soluble $Zn^{++}$ content. The results appear below.

| Sample Time | Product A | Product B | Product C |
|---|---|---|---|
| 12 Day $Zn^{++}$ | 1370 ppm | 301 ppm | 761 ppm |
| 4 Week $Zn^{++}$ | 1290 ppm | 216 ppm | 384 ppm |
| Initial Insolubles/Crystals | none | significant | none |
| 12 Day Insolubles/Crystals | none | significant | some |
| 4 Week Insolubles/Crystals | none | significant | some |

Example 3

Each of the following formulations are prepared using only a source of zinc ion, a source of stabilizing anion, and a bicarbonate source added to 100 grams of water. Clarity is examined the same day as preparation.

| | gms $ZnCl_2$ | gms NaCitrate[†] | gms $NaHCO_3$ | Anion/ $Zn^{++}$ | equivalent ratio $HCO_3^-$/ Anion | solution clarity |
|---|---|---|---|---|---|---|
| a | 0.30 | 0 | 3.00 | 0 | infinite | cloudy |
| b | 0.30 | 0.30 | 3.00 | 0.70 | 11.67 | cloudy |
| c | 0.30 | 0.50 | 3.00 | 1.16 | 7.00 | cloudy |
| d | 0.30 | 0.70 | 3.00 | 1.62 | 5.00 | clear |
| e | 0.30 | 0.70 | 6.00 | 1.62 | 10.00 | cloudy |
| f | 0.30 | 1.00 | 3.00 | 2.32 | 3.50 | clear |
| g | 0.30 | 1.00 | 6.00 | 2.32 | 7.00 | clear |
| h | 0.30 | 1.00 | 8.00 | 2.32 | 9.34 | cloudy |

[†]as dihydrate

Example 4

Example 3 is repeated except that differing zinc sources and differing stabilizing anions are used as indicated in the tables.

TABLE I

Citrate as Stabilizing Anion

|   | gms ZnCitrate* | gms NaCitrate† | gms NaHCO$_3$ | Anion/ Zn$^{++}$ | HCO$_3^-$/ Anion | solution clarity |
|---|---|---|---|---|---|---|
| a  | 0.5 | 0.00 | 4.00 | 1.00 | 9.97  | cloudy |
| b  | 0.5 | 0.10 | 4.00 | 1.21 | 8.22  | cloudy |
| c. | 0.5 | 0.30 | 4.00 | 1.64 | 6.08  | clear |
| d. | 0.5 | 0.30 | 6.00 | 1.64 | 9.12  | cloudy |
| e  | 0.5 | 0.50 | 4.00 | 2.07 | 4.82  | clear |
| f  | 0.5 | 0.50 | 6.00 | 2.07 | 7.23  | clear |
| g  | 0.5 | 0.50 | 7.00 | 2.07 | 8.44  | clear |
| h  | 0.5 | 0.50 | 9.00 | 2.07 | 10.85 | cloudy |
| i  | 0.5 | 0.70 | 4.00 | 2.50 | 4.00  | clear |

*as trihydrate
†as dihydrate

TABLE II

Citrate/STPP as Stabilizing Anion

|   | gms ZnCitrate* | gms STPP | gms NaHCO$_3$ | solution clarity |
|---|---|---|---|---|
| a | 0.50 | 0.50 | 0 | clear |
| b | 0.50 | 0.50 | 4 | clear |
| c | 0.50 | 0.50 | 6 | clear |
| d | 0.50 | 0.50 | 7 | cloudy |

*as trihydrate

TABLE III

Citrate/EDTA as Stabilizing Anion

|   | gms ZnCitrate* | gms EDTA | gms NaHCO$_3$ | solution clarity |
|---|---|---|---|---|
| a | 0.50 | 0.37 | 0 | clear |
| b | 0.50 | 0.37 | 4 | clear |
| c | 0.50 | 0.37 | 6 | v. cloudy |

*as trihydrate

TABLE IV

Citrate/Tartrate as Stabilizing Anion

|   | gms ZnCitrate* | gms NaTartrate† | gms NaHCO$_3$ | solution clarity |
|---|---|---|---|---|
| a | 0.50 | 1.00 | 0 | clear |
| b | 0.50 | 1.00 | 4 | clear |
| c | 0.50 | 1.00 | 6 | v. cloudy |

*as trihydrate
†as dihydrate

Example 5

Example 4 is repeated using anions which are not within the present invention.

| zinc source | gms amount | anion | gms amount | gms NaHCO$_3$ | solution clarity |
|---|---|---|---|---|---|
| citrate*  | 0.5  | sulfate   | 2.00 | 4 | v cloudy |
| chloride  | 0.3  | chloride  | 0.6  | 3 | v. cloudy |
| chloride  | 0.3  | sulfate   | 1.00 | 3 | v. cloudy |
| gluconate | 1.75 | gluconate | 2.00 | 5 | v. cloudy |

*as trihydrate

I claim:

1. A storage clarity-stable aqueous or aqueous/alcoholic mouthwash solution of zinc ions in the presence of bicarbonate ions which results from providing, in a single solution, a combination consisting essentially of:
   (a) a zinc ion source which is a zinc salt of a first anion which salt is selected from the group consisting of
      (i) salts of zinc with one or more of said first anion, including mixed first anion salts thereof, said first anion being selected from the group consisting of
         (1) chloride, sulfate, monophosphate, pyrophosphate, metaphosphate, tripolyphosphate, tetrametaphosphate, orthophosphate, and
         (2) organic carboxylic acid anions selected from the group consisting of gluconate, tartrate, fumarate, maleate, malonate, malate, lactate, citrate, EDTA, citraconate, citramalate, stearate, oleate, laurate, octoate ascorbate, picolinate, and orotate, and
      (ii) salts of mixed alkali metal/zinc or mixed magnesium/zinc with said first anion;
   (b) a source of a stabilizing anion which stabilizes solutions of zinc ions in the presence of bicarbonate ions, which source is a salt of a first metal and a second anion, said first metal being selected from the group consisting of sodium and potassium and said second anion being selected from the group consisting of (i) carboxylic acids selected from the group consisting of tartrate, fumarate, maleate, malonate, malate, citraconate, citramalate, lactate, citrate, and EDTA, and (ii) phosphates selected from the group consisting of pyrophosphate and tripolyphosphate;
   (c) a bicarbonate ion source selected from the group consisting of sodium bicarbonate and potassium bicarbonate;
   (d) a solvent therefor, said solvent comprising:
      (i) a major proportion of water;
      (ii) optionally a minor amount of a lower all monohydric alcohol; and
      (iii), optionally a minor amount of a humectant having at least 3 hydroxy groups;
   (e) optionally one or more mouthwash acceptable antibacterial agents;
   (f) optionally one or more mouthwash acceptable viscosity enhancers;
   (g) optionally one or more sweeteners;
   (h) optionally one of more flavors; and
   (i) optionally one or more colors;
   said zinc salt being present in an amount A sufficient to yield a zinc ion concentration of from about 0.01 to about 1 weight %;
   said salt of said second anion present in an amount B, which in combination with any of said second anion present from other components of said solution, is sufficient to provide a total second anion concentration of at least 1.2 equivalents per equivalent of zinc ion;
   said bicarbonate source being present in an amount of C equivalents, which is no greater than the sum of (a) 6×(the number of equivalents of said pyrophosphate and tripolyphosphate); and
(b) $\{(3^{(n-1)})/(2^m)\}$×(the number of equivalents of said second anions which are carboxylic acids), where n is the number of carboxyl groups and m is the number of basic nitrogens whereby said storage clarity-stable aqueous or aqueous/alcoholic single phase mouthwash solution remains clear and free of cloudiness or insoluble crystals or basic salts of zinc and carbonate during storage, said zinc ions and said bicarbonate ions being provided in amounts which are effective for the prevention and counteraction of oral malodors, said bicarbonate ions providing a clean mouthfeel and a refreshing aftertaste in the oral cavity, and said zinc ions combating oral malodor.

2. The solution of claim 1 wherein said first anion is selected from the group consisting of chloride, sulfate, gluconate, tartrate, fumarate, maleate, malonate, lactate, citrate, EDTA, citraconate, citramalate, stearate, oleate, laurate, and octoate.

3. The solution of claim 2 wherein said first anion is citrate.

4. The solution of claim 2 wherein said zinc salt of said first anion is zinc citrate trihydrate.

5. The solution of claim 1 wherein said second anion is selected from the group of consisting of tripolyphosphate, pyrophosphate, fumarate, tartrate, maleate, malonate, citraconate, citramalate, lactate, citrate, and EDTA ion.

6. The solution of claim 5 wherein said second anion is citrate.

7. The solution of claim 5 wherein said salt of said first metal and said second anion is sodium citrate.

8. The solution of claim 7 wherein said sodium citrate is sodium citrate dihydrate.

9. The solution of claim 1 wherein said first anion and said second anion are the same.

10. The solution of claim 1 wherein said alkali metal bicarbonate is sodium bicarbonate.

11. The solution of claim 1 wherein said first metal and the cation of said alkali metal bicarbonate are the same.

12. A storage clarity-stable aqueous or aqueous/alcoholic single phase mouthwash solution of zinc ions in the presence of bicarbonate ions comprising:
(a) a zinc salt of a first anion which salt is selected from the group consisting of
  (i) salts of zinc with one or more of said first anion, including mixed first anion salts thereof, said first anion being selected from the group consisting of
    (1) chloride, sulfate, monophosphate, pyrophosphate, metaphosphate, tripolyphosphate, tetrametaphosphate, orthophosphate, and
    (2) organic carboxylic acid anions selected from the group consisting of gluconate, tartrate, fumarate, maleate, malonate, malate, lactate, citrate, EDTA, citraconate, citramalate, stearate, oleate, laurate, octoate ascorbate, picolinate, and orotate, and
  (ii) salts of mixed alkali metal zinc or mixed magnesium zinc with said first anion;
(b) a salt of a first metal and a second anion, said first metal being selected from the group consisting of sodium and potassium and said second anion being selected from the group consisting of (i) carboxylic acids selected from the group consisting of tartrate, fumarate, maleate, malonate, malate, citraconate, citramalate, lactate, citrate, and EDTA, and (ii) phosphates selected from the group consisting of pyrophosphate and tripolyphosphate;
(c) at least one alkali metal bicarbonate selected from the group consisting of sodium bicarbonate and potassium bicarbonate;
(d) a solvent therefor, said solvent comprising:
  (i) a major proportion of water,
  (ii) optionally a minor amount of a lower alkyl monohydric alcohol; and
  (iii) optionally a minor amount of a humectant having at least 3 hydroxy groups;
(e) optionally one or more mouthwash acceptable antibacterial agents;
(f) optionally one or more mouthwash acceptable viscosity enhancers;
(g) optionally one or more sweeteners;
(h) optionally one of more flavors; and
(i) optionally one or more colors;

said zinc salt being present in an amount A sufficient to yield a zinc ion concentration of from about 0.01 to about 1 weight %;

said salt of said second anion present in an amount B, which in combination with any of said second anion present from other components of said solution, is sufficient to provide a total second anion concentration of at least 1.2 equivalents per equivalent of zinc ion;

said at least one alkali metal bicarbonate being present in an amount of C equivalents, which is no greater than the sum of
(a) 6×(the number of equivalents of said pyrophosphate and tripolyphosphate); and
(b) $\{(3^{(n-1)})/(2^m)\}$×(the number of equivalents of said second anions which are carboxylic acids), where n is the number of carboxyl groups and m is the number of basic nitrogens, whereby said storage clarity-stable aqueous or aqueous/alcoholic single phase mouthwash solution remains clear and free of cloudiness or insoluble crystals or basic salts of zinc and carbonate during storage, said zinc ions and said bicarbonate ions being provided in amounts which are effective for the prevention and counteraction of oral malodors, said bicarbonate ions providing a clean mouthfeel and a refreshing aftertaste in the oral cavity, and said zinc ions combating malodor.

13. A method of preparing a storage clarity-stable aqueous or aqueous/alcoholic mouthwash solution consisting essentially of:
(a) a zinc ion source which is a zinc salt of a first anion which salt is selected from the group consisting of
  (i) salts of zinc with one or more of said first anion, including mixed first anion salts thereof, said first anion being selected from the group consisting of
    (1) chloride, sulfate, monophosphate, pyrophosphate, metaphosphate, tripolyphosphate, tetrametaphosphate, orthophosphate, and
    (2) organic carboxylic acid anions selected from the group consisting of gluconate, tartrate, fumarate, maleate, malonate, malate, lactate, citrate, EDTA, citraconate, citramalate, stearate, oleate, laurate, octoate ascorbate, picolinate, and orotate, and
  (ii) salts of mixed alkali metal/zinc or mixed magnesium/zinc with said first anion;
(b) a source of a stabilizing anion which stabilizes solutions of zinc ions in the presence of bicarbonate ions, which source is a salt of a first metal and a second anion, said first metal being selected from the group consisting of sodium and potassium and said second anion being selected from the group consisting of (i) carboxylic acids selected from the group consisting of tartrate, fumarate, maleate, malonate, malate, citraconate, citramalate, lactate, citrate, and EDTA, and (ii) phosphates selected from the group consisting of pyrophosphate and tripolyphosphate;

(c) a bicarbonate ion source selected from the group consisting of sodium bicarbonate and potassium bicarbonate;

(d) a solvent therefor, said solvent comprising:
(i) a major proportion of water;
(ii) optionally a minor amount of a lower alkyl monohydric alcohol; and
(iii) optionally a minor amount of a humectant having at least 3 hydroxy groups;

(e) optionally one or more mouthwash acceptable antibacterial agents;

(f) optionally one or more mouthwash acceptable viscosity enhancers;

(g) optionally one or more sweeteners;

(h) optionally one of more flavors; and (i) optionally one or more colors;

said zinc salt being present in an amount A sufficient to yield a zinc ion concentration of from about 0.01 to about 1 weight %;

said salt of said second anion present in an amount B, which in combination with any of said second anion present from other components of said solution, is sufficient to provide a total second anion concentration of at least 1.2 equivalents per equivalent of zinc ion;

said bicarbonate source being present in an amount of C equivalents, which is no greater than the sum of
(a) (6)×(the number of equivalents of said pyrophosphate and tripolyphosphate); and
(b) $\{(3^{(n-1)})/(2^m)\}$×(the number of equivalents of said second anions which are carboxylic acids), where n is the number of carboxyl groups and m is the number of basic nitrogens whereby said storage clarity-stable aqueous or aqueous/alcoholic single phase mouthwash solution remains clear and free of cloudiness or insoluble crystals or basic salts of zinc and carbonate during storage, said zinc ions and said bicarbonate ions being provided in amounts which are effective for the prevention and counteraction of oral malodors, said bicarbonate ions providing a clean mouthfeel and a refreshing aftertaste in the oral cavity, and said zinc ions combating oral malodor said method comprising
contacting said stabilizing amount of said stabilizing anion with said zinc ions and said bicarbonate ions.

14. The method of claim 13 wherein said stabilizing anions are contacted with said zinc ions prior to the addition of said bicarbonate ions.

* * * * *